United States Patent
Bhattacharya

(10) Patent No.: US 11,096,648 B2
(45) Date of Patent: Aug. 24, 2021

(54) CALIBRATION BIAS REDUCTION IN A PRESSURIZED GAS ION CHAMBER-BASED DOSE CALIBRATOR

(71) Applicant: Siemens Medical Solutions USA, Inc., Malvern, PA (US)

(72) Inventor: Manojeet Bhattacharya, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/733,431

(22) PCT Filed: Jan. 22, 2019

(86) PCT No.: PCT/US2019/014440
§ 371 (c)(1),
(2) Date: Jul. 29, 2020

(87) PCT Pub. No.: WO2019/172997
PCT Pub. Date: Sep. 12, 2019

(65) Prior Publication Data
US 2021/0093283 A1    Apr. 1, 2021

Related U.S. Application Data

(60) Provisional application No. 62/639,649, filed on Mar. 7, 2019.

(51) Int. Cl.
*A61B 6/00* (2006.01)
*A61B 6/03* (2006.01)

(52) U.S. Cl.
CPC .............. *A61B 6/542* (2013.01); *A61B 6/037* (2013.01); *A61B 6/582* (2013.01)

(58) Field of Classification Search
CPC ......... A61B 6/542; A61B 6/582; A61B 6/037; A61B 6/4258; A61B 6/461; A61B 6/52; G01T 1/1647; G01T 1/161; G01T 1/171
See application file for complete search history.

(56) References Cited

U.S. PATENT DOCUMENTS 5,491,342 A * 2/1996 Lim ................. G01T 1/1648
250/252.1
8,615,405 B2 * 12/2013 Rousso ................ A61B 6/037
705/2

(Continued)

FOREIGN PATENT DOCUMENTS

WO      2018052447 A1     3/2018

OTHER PUBLICATIONS

International Search Report for corresponding application No. PCT/US2019/014440, dated Apr. 11, 2019.

*Primary Examiner* — David P Porta
*Assistant Examiner* — Djura Malevic

(57) ABSTRACT

For dose calibration (39) in functional imaging, different precision sources (22, 25) for a same long-lived isotope are used to calibrate, avoiding having to ship one source from one location to another location. A ratio of sensitivities of a gas ion chamber-based dose calibrator (20) at a reference laboratory to the precision source (22) of the long-lived isotope to a source (23) with an isotope to be used for imaging is found. At the clinical site (e.g., radio-pharmacy or functional imaging facility), a measure (34) of the sensitivity of a local gas ion chamber-based dose calibrator (24) to the other source (25) with the long-lived isotope and the ratio from the remote gas ion chamber-based dose calibrator (20) are used to determine sensitivity of the local gas ion chamber-based dose calibrator (24) to the isotope of the radiopharmaceutical (26). The bias and corresponding dose for the radiopharmaceutical (26) to be used for imaging a (Continued)

patient are based on activity for the radiopharmaceutical (26) as calibrated to account for the sensitivity of the local gas ion chamber-based dose calibrator (24) to the isotope of the radiopharmaceutical (26).

20 Claims, 3 Drawing Sheets

(56) References Cited

U.S. PATENT DOCUMENTS

| | | | | |
|---|---|---|---|---|
| 9,364,192 B2* | 6/2016 | Vija | ............... | A61B 6/5258 |
| 9,504,431 B2* | 11/2016 | Bhattacharya | ......... | A61B 6/037 |
| 9,739,894 B2* | 8/2017 | Bhattacharya | ......... | G01T 1/161 |
| 9,867,581 B2* | 1/2018 | Bhattacharya | ......... | A61B 6/037 |
| 9,910,162 B2* | 3/2018 | Bhattacharya | ......... | G01T 1/166 |
| 10,245,002 B2* | 4/2019 | Bhattacharya | ......... | A61B 6/582 |
| 10,670,745 B1* | 6/2020 | Catarius | ............... | G01T 7/005 |
| 10,820,880 B2* | 11/2020 | Bhattacharya | ......... | A61B 6/582 |
| 11,020,083 B2* | 6/2021 | Ding | ............... | G01T 1/1647 |
| 2007/0040115 A1* | 2/2007 | Publicover | ............ | G01T 1/29 |
| | | | | 250/305 |
| 2008/0042067 A1* | 2/2008 | Rousso | ............... | G01T 1/161 |
| | | | | 250/363.04 |
| 2008/0056550 A1* | 3/2008 | Kadir | ............... | G06T 11/006 |
| | | | | 382/131 |
| 2008/0075344 A1* | 3/2008 | Nambu | ............... | G06T 5/009 |
| | | | | 382/131 |
| 2009/0110256 A1* | 4/2009 | Thielemans | ............ | G06T 7/30 |
| | | | | 382/131 |
| 2009/0127449 A1* | 5/2009 | Iwatschenko-Borho | ............... | |
| | | | | G01T 1/40 |
| | | | | 250/252.1 |
| 2009/0194677 A1 | 8/2009 | Allberg | | |
| 2009/0208075 A1* | 8/2009 | Fischer | ............... | G06T 7/11 |
| | | | | 382/128 |
| 2010/0046818 A1* | 2/2010 | Yamaya | ............... | G01T 1/1648 |
| | | | | 382/131 |
| 2010/0174180 A1* | 7/2010 | Rousso | ............... | A61B 6/037 |
| | | | | 600/431 |
| 2011/0044524 A1* | 2/2011 | Wang | ............... | G01R 33/54 |
| | | | | 382/131 |
| 2011/0147594 A1* | 6/2011 | Scoullar | ............... | G01T 1/171 |
| | | | | 250/362 |
| 2011/0164801 A1* | 7/2011 | Gagnon | ............... | G01R 33/481 |
| | | | | 382/131 |
| 2012/0326034 A1* | 12/2012 | Sachs | ............... | G06T 11/005 |
| | | | | 250/336.1 |
| 2014/0371580 A1* | 12/2014 | Bhattacharya | ......... | A61B 6/582 |
| | | | | 600/426 |
| 2015/0196268 A1* | 7/2015 | Bhattacharya | ......... | A61B 6/037 |
| | | | | 600/425 |
| 2015/0297168 A1* | 10/2015 | Panin | ............... | A61B 6/037 |
| | | | | 600/427 |
| 2016/0356894 A1* | 12/2016 | Bhattacharya | ......... | G01T 1/161 |
| 2017/0042500 A1* | 2/2017 | Bhattacharya | ......... | G01T 7/005 |
| 2017/0065732 A1 | 3/2017 | Srinivas et al. | | |
| 2017/0188982 A1* | 7/2017 | Bhattacharya | ......... | G01T 1/171 |
| 2017/0192014 A1 | 7/2017 | Miller et al. | | |
| 2017/0192104 A1* | 7/2017 | Bhattacharya | ............ | G01T 1/40 |
| 2018/0092609 A1* | 4/2018 | Bhattacharya | ......... | A61B 6/037 |
| 2018/0092610 A1* | 4/2018 | Bhattacharya | ......... | A61B 6/037 |
| 2019/0038252 A1* | 2/2019 | Bhattacharya | ......... | A61B 6/582 |

* cited by examiner

Gamma and X-ray radiation:

| | Energy (keV) | Intensity (%) | Dose (MeV/Bq-s) | |
|---|---|---|---|---|
| XR l | 3.13 | 6.78 % 17 | 2.12E-4 5 | ⎫ |
| XR kα2 | 22.984 | 24.1 % 7 | 0.00553 16 | ⎪ |
| XR kα1 | 23.174 | 45.3 % 13 | 0.0105 3 | ⎬ Characteristic X-rays |
| XR kβ3 | 26.06 | 3.92 % 11 | 0.00102 3 | ⎪ |
| XR kβ1 | 26.095 | 7.55 % 22 | 0.00197 6 | ⎪ |
| XR kβ2 | 26.644 | 1.94 % 6 | 5.18E-4 16 | ⎭ |
| | 150.81 3 | 0.0030 % 3 | 4.5E-6 5 | |
| | 171.28 3 | 90.7 % 9 | 0.1553 16 | ⎱ Gamma Emissions |
| | 245.35 4 | 94.1 % 10 | 0.2308 24 | ⎰ |

Gamma Coincidence Data   FIG. 1 (Prior Art)

CALIBRATION BIAS REDUCTION IN A PRESSURIZED GAS ION CHAMBER-BASED DOSE CALIBRATOR

RELATED APPLICATIONS

The present patent document claims the benefit of the filing date under 35 U.S.C. § 119(e) of Provisional U.S. Patent Application Ser. No. 62/639,649, filed Mar. 7, 2018, which is hereby incorporated by reference.

BACKGROUND

The present embodiments relate to dose calibration for functional imaging. Dose calibration is provided for quantitative or other functional imaging.

Positron emission tomography (PET) and single photon emission computed tomography (SPECT) are two types of functional or nuclear imaging. Functional imaging uses a radioisotope or radiotracer to determine metabolic function within a patient. The emissions from the radiotracer are detected. The activity concentration (i.e., the concentration of the radiotracer from different locations) is reconstructed from the detected emissions. For quantitative functional imaging, both accurate activity concentration and uptake values are desired. The goal is to provide a global baseline that is free of system (detector and dose calibrator) variability so that any measured change for a patient over time in either quantity is due to metabolic reasons. The injected activity is an important quantity not only for the sake of adhering to the prescribed dose but also for use in computing uptake values in quantitative functional imaging.

A gas ion chamber-based dose calibrator provides a measurement of the dose. The dose value for the liquid isotope (radiotracer or radiopharmaceutical) applied to the patient may be inaccurate. One source of inaccuracy is contribution from characteristic X-rays. FIG. 1 shows a table of emission spectrum for $In^{111}$. The table includes energy, the intensity (with % chance of occurring in a given instance of decay and the uncertainty), and the dose for gamma and X-ray emissions. The gas ion chamber-based dose calibrator sensitivity is a highly non-linear function of incident photon or gamma energy. Primary gamma emissions from many SPECT radiotracers are at the minimum of the chamber sensitivity while chamber sensitivity for characteristic X-ray energies of the SPECT radiotracers is high. As a result, the gas ion chamber-based dose calibrator measurement of activity includes a larger or comparable amount of energy from X-rays. The injected activity when assayed has a large bias for the isotopes that emit X-rays in addition to the imaging photons. For SPECT radiotracers with high energy gamma emissions in addition to the primary emissions, multiple Compton scattering of the higher energy gamma rays also results in dose uncertainty.

To limit energy contribution from characteristic X-rays in dose calibration, a passive shield (e.g., copper jacket) is introduced to differentially attenuate the X-rays relative to the primary emissions. The jacket reduces but does not eliminate the X-rays, attenuates the primary emissions, and has unknown production tolerances, resulting in uncertainties of varying magnitude. For isotopes with significant emissions of X-rays, the differential attenuation of the X-rays and gamma-rays in the tracer container also creates uncertainty. For isotopes with high energy gamma emissions in addition to primary emissions, the higher efficiency for high energy gamma-rays due to multiple Compton scattering results in dose uncertainty.

In another approach, an isotope source in a standard geometry is calibrated using an efficiency calibrated HPGe detector. The primary emissions and well-known branching ratio are used to calibrate the same source in a gas ion chamber-based dose calibrator, allowing determination of the bias. However, it is logistically challenging to manufacture and ship the source between sites due to the radioactivity.

SUMMARY

By way of introduction, the preferred embodiments described below include methods, systems, and non-transitory computer readable media for dose calibration in functional imaging. Different precision sources for a same long-lived isotope are used to calibrate, avoiding having to ship one source from one location to another location. A ratio of sensitivities of a dose calibrator at a reference laboratory to the precision source of the long-lived isotope to a source with an isotope to be used for imaging is found. At the clinical site (e.g., radio-pharmacy or functional imaging facility), a measure of the sensitivity of a local gas ion chamber-based dose calibrator to the other source with the long-lived isotope and the ratio from the remote dose calibrator are used to determine sensitivity of the local dose calibrator to the isotope of the radiopharmaceutical. The bias and corresponding dose for the radiopharmaceutical to be used for imaging a patient are based on activity for the radiopharmaceutical as calibrated to account for the sensitivity of the local dose calibrator to the isotope of the radiopharmaceutical.

In a first aspect, a method is provided of dose calibration for a functional imaging system. A first activity for a first source of a first isotope is measured with a first dose calibrator at a first location, and a first dial setting is determined from the first activity. A second activity of a second source of a second isotope is measured with the first dose calibrator at the first location. The second isotope is relatively shorter lived than the first isotope. A second dial setting is determined from the second activity. A third activity of a third source of the first isotope is measured with a second dose calibrator at a second location. The second location is a clinical or pharmaceutical site different than the first location. A third dial setting is determined from the third activity. A fourth dial setting is determined for a radiopharmaceutical of the second isotope from the third dial setting and a ratio of the first dial setting to the second dial setting. A fourth activity of the radiopharmaceutical is measured using the fourth dial setting, and the fourth activity is used to calibrate.

In a second aspect, a method is provided of dose calibration for a functional medical imaging system. A first activity of a first source of a first isotope is measured with a first dose calibrator at a clinical or pharmaceutical site. A first sensitivity of the first dose calibrator to the first isotope is determined from the first activity and a reference activity of the first source. A second sensitivity of the first dose calibrator to a second isotope is determined from the first sensitivity and a ratio of third and fourth sensitivities of a second dose calibrator to the first isotope and the second isotope, respectively. A radiopharmaceutical activity of a radiopharmaceutical of the second isotope is measured with the second sensitivity.

In a third aspect, a system is provided for calibration of dose in functional imaging. A first dose calibrator is provided for measuring activity of a radiotracer source and activity of a radiopharmaceutical. A processor is configured to determine a bias of the activity of the radiopharmaceutical by the first dose calibrator from (1) a first dial setting of the dose calibrator determined from the activity of the radiotracer source and a reference activity for the radiotracer source and (2) a ratio of second and third dial settings for an isotope of the radiotracer source to isotope of the radiopharmaceutical.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a table showing the emission spectrum for $In^{111}$;

DETAILED DESCRIPTION OF THE DRAWINGS AND PRESENTLY PREFERRED EMBODIMENTS

Multiple long-lived isotope reference sources are used for isotope-specific calibration of a pressurized gas ion chamber-based dose calibrator. Precision long-lived isotope sources and relative calibration allow for dose calibration. The precision reference sources of a long-lived isotope in fixed geometry along with a short-lived isotope in a precisely fabricated low attenuating container of fixed geometry are used to determine a relative chamber sensitivity of a reference dose calibrator at a reference lab. The relative chamber sensitivity and a reference source chamber sensitivity measurement at a clinical site are used to derive a local chamber sensitivity for a short-lived isotope. The calibration bias of the local dose calibrator is reduced or eliminated by using a secondary precision calibration source with a long-lived isotope that emits photon of energy that is close to the energy of the photons emitted by the radio pharmaceutical. Uncertainty from a copper sleeve and the logistics transporting the precision short-lived liquid source to remote sites are avoided.

Figure 2:
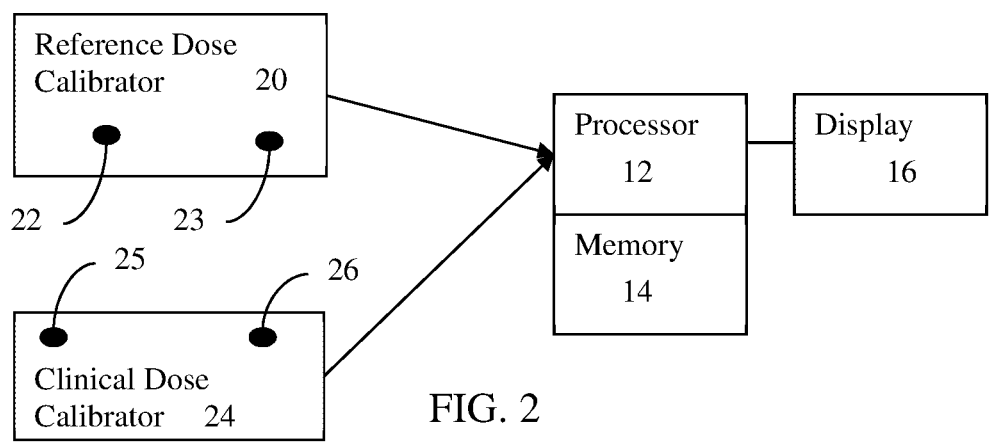
FIG. 2 is a block diagram of one embodiment of a system for calibration of dose.

FIG. 2 shows one embodiment of a system for calibration of dose in functional imaging, such as SPECT quantification imaging of uptake values. The bias in a dose measurement from a local or clinical gas ion chamber-based dose calibrator is determined based on a ratio of sensitivities of another gas ion chamber-based dose calibrator to two isotopes. The bias may be used to correct the dose provided by dose calibrators for any purpose, such as to calibrate PET or SPECT imaging and/or to calculate uptake values for quantitative functional imaging.

Figure 5:
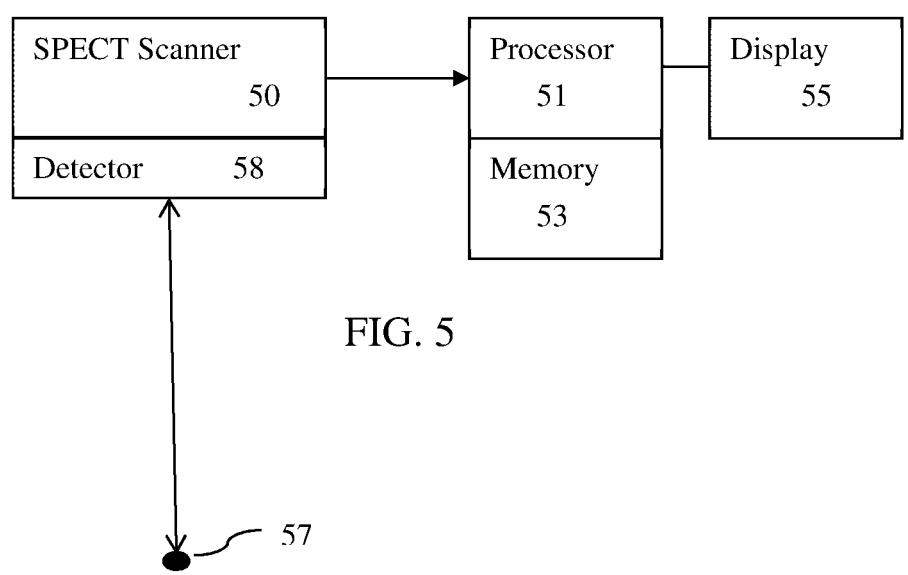
FIG. 5 is a block diagram of a SPECT system, according to one embodiment, for use of corrected dose in quantitative or other functional imaging.

The system of FIG. 2 is directed to determining the bias, and the system of FIG. 5 is directed to use of the bias or bias corrected dose. The system of FIG. 2 implements part of the method of FIG. 3 (e.g., acts 30-38 or 30-39). Different methods may be implemented.

The system includes a reference dose calibrator 20, a clinical dose calibrator 24, a processor 12, a memory 14, and a display 16. Additional, different, or fewer components may be provided. For example, the memory 14 and/or display 16 are not provided. As another example, a SPECT system, PET system, spectroscopic detector, and/or a user interface (user input device and display 16) are provided.

In one embodiment, the system determines the biases for different radioisotopes and/or geometries. A table of biases as a function of isotope and/or geometry is provided to one or more functional imaging systems. For determining biases, a ratio of dial settings or sensitivity corrections of the reference dose calibrator 20 or table of such ratios for different combinations of isotopes and/or geometries are provided by a manufacturer or other reference laboratory. For each bias, two reference sources 22, 23 with referenced doses are used to determine the ratio using measurements from the reference dose calibrator 20. The clinical (e.g., radio-pharmacy site that dispense dosage for patient imaging by a functional imaging system or site of the functional imaging system) has a reference source 25 with a known or referenced dose. Rather than shipping a source 22, 23 to the clinical or radio-pharmacy site, the reference source 25 is used with the ratio from the reference site to determine the sensitivity, bias, or dial setting for the clinical dose calibrator 24 for the radiopharmaceutical being prepared for a patient. The functional imaging system or the clinical site determines a calibrated dose for the provided radiopharmaceutical by applying the appropriate bias (e.g., adjustment for the sensitivity or dial setting) to the clinical dose calibrator 24 provided dose or activity value. This corrected dose value may provide for more accurate activity concentration measurements and/or specific uptake value (SUV) calculations.

For determining the bias for a given isotope of a radiopharmaceutical 26, the reference radiotracer sources 22, 23, and 25 are used. One reference source 22 at the reference laboratory and one radiotracer source 25 at the clinical site are of a long-lived isotope. The sources 22, 25 use the same isotope. Long-lived isotopes have a half life of six months, one year, two years, or any period greater than six months, one year, or two years. Any isotope may be included in the long-lived radiotracer sources 22, 25, such as $Co^{57}$, $Se^{75}$, or $Sn^{113}$, $Ge^{68}$ One reference source 23 at the reference laboratory has a same isotope used in the radiopharmaceutical 26. This isotope is a relatively short-lived isotope, so has a half life less than the half life of the long-lived isotopes of the radiotracer sources 22, 25. The short-lived isotopes have a half life of less than six months, such as one month, one week, two days, one day, or less than one month, one week, two day, or one day. Any isotope may be included in the short-lived reference source 23 and radiopharmaceutical 26, such as $In^{111}$, $I^{123}$, $I^{125}$, $Xe^{133}$, or $Ce^{139}$, Lu177, I123, I131, Tc99, F18, Ga68.

The radiopharmaceutical 26 includes the pharmaceutical for binding to or attraction to functional (e.g., metabolic) processes in the patient tissue. The short-lived isotope is also included. Alternatively, the radiopharmaceutical 26 includes the isotope without the pharmaceutical having been added at the time of clinical dose calibrator 24 measurement.

The sources 22, 23, 25, and/or 26 are packaged with any geometry. For example, the radiotracer is in a syringe. As another example, the liquid isotope is encased in a metal or plastic housing of any shape. The size, shape, and/or material of the housing defines the geometry. Low attenuating material, such as plastic, is used for the short-lived isotopes. The volume of the container for the short-lived sources 23 and/or 26 may be the same or similar to volumes used for bulk, unit dose, and/or patient prescriptions of the radiopharmaceutical 26. The geometry is preferably one of commonly used geometries for radiotracers provided for functional imaging, such as a liquid radiotracer in a plastic syringe. The material, shape, and volume for the long-lived sources 22 and/or 25 is the same or different than for the short-lived sources 23 and/or 26 and/or each other.

The reference and clinical dose calibrators 20, 24 include a fixed geometry for measurement. A plastic or other material form or piece may position the sources 22, 23, 25, and/or 26 at specific or fixed locations within the reference and clinical dose calibrators 20, 24, providing a fixed geometry for measurement.

The long-lived isotope sources 22, 25 have a known or reference activity or dose. The reference laboratory (e.g., manufacturer of the liquid isotope) indicates an accurate or reference activity. For example, a spectroscopic detector, such as a solid-state detector of gamma rays having a scintillation crystal with a contact diode for sensing light generated by gamma ray interaction with the crystal, is used. In one embodiment, a high-purity or other Germanium (HPGe) detector is used. A cylinder of Germanium is cooled, and a voltage is applied. The source 22 or 25 is positioned at one end and gamma emissions are detected with an anode and cathode arrangement in the Ge semiconductor. Other spectroscopic detectors may be used, such as based on a photo-multiplier tube. The short-lived isotope reference source 23 likewise has a reference activity or dose. The reference laboratory indicates the accurate or reference activity using a spectroscopic detector.

The same or different spectroscopic detectors measure activity of the radiotracer sources 22, 23, and 25. Electrical signals generated by the photon or gamma emissions interaction with the spectroscopic detector are measured. This measure provides a dose or activity. The spectroscopic detector is calibrated and capable of measuring emissions at different energies. Emissions at each energy may be separately measured, such as measuring at primary emission energies and not X-ray energies.

The reference and clinical dose calibrators 20, 24 are pressurized gas dose calibrators, such as a pressurized ion gas chamber dose calibrators. A pressurized gas is housed in a gap between two concentric cylinders or other shapes. The sources 22, 23, 25, 26 are positioned in the inner cylinder of the reference or clinical dose calibrators 20, 24 at different times. Emissions from the radiotracer source 22, 23, 25, or 26 that reach the gas may interact with the gas, creating an ion-electron pair. A voltage is applied across or between the cylinders, which act as an anode and a cathode. The energy from the ion-electron pairs is measured, providing the activity or dose of the isotope source 22, 23, 25, and/or 26.

The gas ion chamber-based dose calibrators 20, 24 measure activity of the isotope sources 22, 23, 25, 26. Electrical signals generated by the interaction of the emitted gamma rays with the pressurized gas are measured. This measure provides a dose or activity. The dose calibrators 20, 24 are calibrated and measure all emissions that interact with the gas. The dose calibrators 20, 24 are different types of activity measuring system than spectroscopic detectors.

The reference dose calibrator 20 measures the activity or dose of the long-lived and short-lived isotopes of the reference sources 22 and 23. The clinical dose calibrator 24 measures the activity or dose of the long-lived and short-lived isotopes of the clinical sources 25 and 26 (e.g., the precision long-lived isotope source 25 and the radiopharmaceutical 26 to be used for imaging a patient).

The reference dose calibrator 20 performs the measurement at a facility remote or different (e.g., different building, city, state and/or country) than the clinical dose calibrator 24. For example, the reference dose calibrator 20 is at a reference laboratory that has the spectroscopic detector, at a manufacturer, or at a facility for providing reference information. The clinical dose calibrator 24 is at a clinical location, such as a radio-pharmacy for dispensing and/or manufacturing the radiopharmaceutical 26 for use with a patient or the hospital or other facility at which the radiopharmaceutical 26 is to be injected into the patient and/or used to image.

The processor 12 is a general processor, digital signal processor, graphics processing unit, application specific integrated circuit, field programmable gate array, digital circuit, analog circuit, combinations thereof, or other now known or later developed device for calibration or dose determination. The processor 12 is a single device, a plurality of devices, or a network. For more than one device, parallel or sequential division of processing may be used. Different devices making up the processor 12 may perform different functions. In one embodiment, the processor 12 is a control processor or other processor of a dose calibrator 24 or functional imaging system. In other embodiments, the processor 12 is part of a separate workstation, server, or computer. The processor 12 is a hardware device that operates pursuant to hardware design, firmware, and/or software stored instructions to perform various acts described herein.

Figure 4:
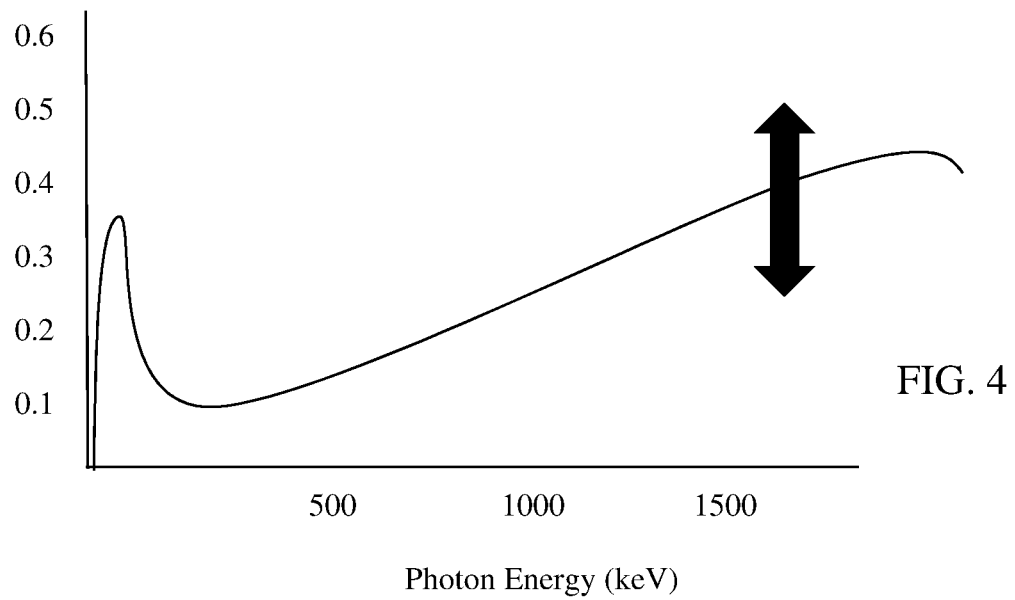
FIG. 4 is an example graph of gas ion chamber-based dose calibrator sensitivity by isotope energy.

The processor 12 is configured to determine a bias of the activity of the radiopharmaceutical 26 measured by the clinical dose calibrator 24. Due to uncertainties, the measure from the clinical dose calibrator 24 includes inaccuracies. For example, FIG. 4 shows a non-linear sensitivity curve for a dose calibrator with different sensitivity levels by energy. The double arrow represents an unknown or uncertain shift of the sensitivity curve as a baseline. Other uncertainties may be reflected, such as the curve having different shape or sensitivity as a function of energy. To calibrate the clinical dose calibrator 24, the bias value for a given isotope or energy is determined. The bias value is used to correct the dose measured by the clinical dose calibrator 24 for radiotracer sources used in patient imaging (i.e., the radiopharmaceutical 26).

The bias is a percentage difference, ratio difference, or other relationship or correction between the measure of activity and an actual activity. For example, the clinical dose calibrator 24 measures the activity or dose of the radiopharmaceutical 26 as 1.5 millicurie. The bias is calculated as a percent difference (i.e., 50%), an offset (e.g., 0.5), or a ratio (e.g., 0.67 or 1.5). Other relationships between the two values may be used. The bias may be a scaling or conversion factor, such as a dial setting. The dial setting is a bias to correct for the dose-calibrator-specific sensitivity at the energy. The clinical dose calibrator 24 may apply the dial setting to output the more accurate activity or dose. Alternatively, another device (e.g., functional imaging system or workstation) applies the bias or dial setting to a measured activity output by the clinical dose calibrator 24.

The value of the bias is used for sensitivity calibration. The bias weights the provided dose, such as by division or multiplication of the dose value by the ratio or percentage difference or adding or subtracting the offset. This bias-corrected dose is used in the calibration of sensitivity for the type or SPECT system. The corrected dose for the radiopharmaceutical measured by that local dose calibrator may be used by the local SPECT system in reconstruction or calculation of specific uptake values or activity concentration. The dose provided by a manufacturer of the radiotracer for a given patient is altered or already includes the bias correction.

The bias is determined for a particular radioisotope and geometry of the radiotracer source or radiopharmaceutical 26. For example, the bias is determined for $In^{111}$ in a glass vial of a given size, shape, and position within the clinical dose calibrator 24. For other isotopes and/or geometries, separate biases are determined.

The bias to be applied depends on the clinical dose calibrator 24. Different clinical dose calibrators 24 may have different biases for a same energy and a given clinical dose calibrator 24 may have different biases for different energies. To remove this uncertainty, a ratio of sensitivities or biases (e.g., dial settings) for one dose calibrator to the long-lived precision source 22 to the short-lived precision source 23 and a measurement of the clinical dose calibrator 24 for a long-lived precision source 25 are used. The precision sources 22, 23, and 25 have known or reference activity, providing for bias determination. To find the bias for the clinical dose calibrator 24 for the isotope of the radiopharmaceutical 26, the ratio from the other dose calibrator (i.e., reference dose calibrator 20) and the bias for the clinical dose calibrator 24 for the precision long-lived source 25 are used.

The bias for the radiopharmaceutical isotope is found as the ratio of the short-lived bias to the long-lived bias of the reference dose calibrator times the bias of the long-lived isotope for the clinical dose calibrator. The processor 12 is configured to determine a bias of the activity of the radiopharmaceutical 26 by the clinical dose calibrator 24 from (1) a dial setting of the clinical dose calibrator 24 determined from the activity of the radiotracer source 25 and the reference activity of that source 25 and (2) a ratio of long-lived and short-lived isotope dial settings for isotopes of the radiotracer source 25 to isotope of the radiopharmaceutical 26, but in different reference sources 22, 23. The ratio is based on measurement from the reference dose calibrator 20 at a reference laboratory, and the biases are found using the known or reference activities based on measurement by a high-purity Germanium or other detector. The sensitivity of the clinical dose calibrator 24 determined based on reference information for energy of the long-lived isotope and the ratio of sensitivities based on reference information for energies of the long and short-lived isotopes are used to determine the sensitivity of the clinical dose calibrator 24 to the short-lived isotope of the radiopharmaceutical 26.

For implementation at the clinical site, a table of different ratios or the ratio to be used is stored in the memory 14. The precision source 25 available at the clinical site is for a given long-lived isotope. The radiopharmaceutical 26 to be used for a given patient is of a given short-lived isotope. The ratio for these two isotopes is looked-up from the table or otherwise accessed. Different tables and/or ratios may be provided for different geometries, so the look-up may also include geometry (e.g., shape of source, size of source, and/or location of source in the dose calibrator 20, 24).

The processor 12 is configured to determine the bias (e.g., dial setting or sensitivity correction) and/or a corrected dose of the radiopharmaceutical 26. The corrected dose is the measured activity calibrated or adjusted for the bias. The bias and/or measured dose from the clinical dose calibrator 24 for the radiopharmaceutical 26 may be stored in the memory 14. A corrected dose value may be stored in the memory 14. Any of the bias, measurements, or dose values may be displayed on the display 16.

The display 16 is a CRT, LCD, plasma, projection, printer, or other display device. The display 16 is configured by data stored in a display plane or buffer to display an image. The image may be of the measured dose, the bias, and/or the corrected dose.

Figure 3:
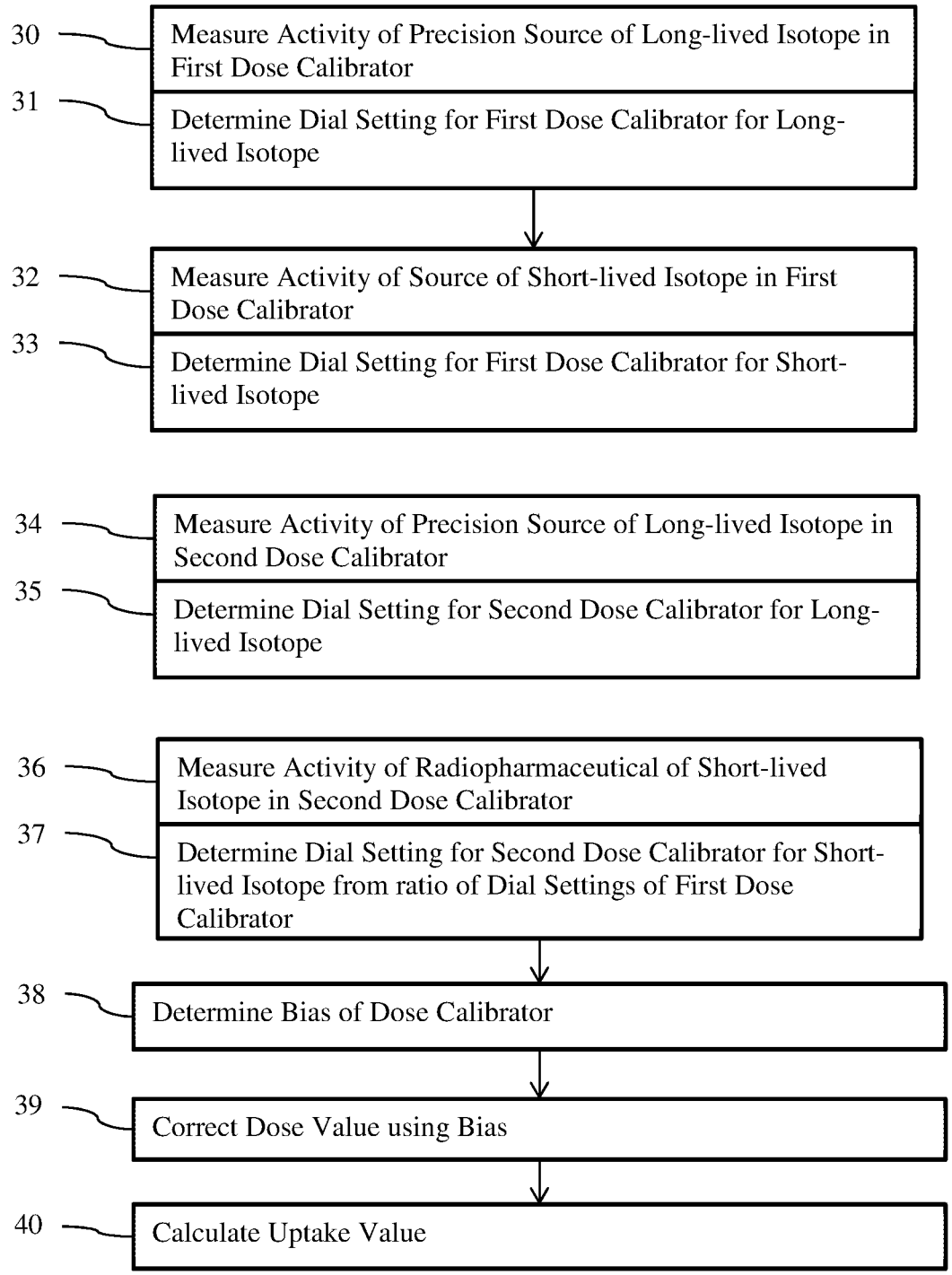
FIG. 3 is a flow chart diagram of one embodiment of a method for dose calibration for nuclear imaging.

FIG. 3 shows one embodiment of a flow chart of a method of dose calibration for a functional imaging system (e.g., SPECT or PET system). The examples below are provided for SPECT but may be used in PET or other functional imaging modality. The dose of a radiopharmaceutical for a patient is calibrated in a way removing or reducing variability by reference measurement for a local precision source and a reference sensitivity ratio for a reference gas ion chamber-based dose calibrator. For activity concentration estimation or uptake calculation (e.g., specific uptake value calculation), the ratio and precision or referenced source are used to determine the sensitivity of the local gas ion chamber-based dose calibrator to the isotope of the radiopharmaceutical.

The method of FIG. 3 is directed to the determination of the bias, the use of the bias for calibration of sensitivity, and use of the calibration for dose correction at a local system. For use, the method is applied for a given scan of a given patient. By applying the method to different scans of the patient, the resulting quantities may be compared and have little to no variance due to differences in dose. The different scans use the same or different detectors and/or doses. Similarly, the SUV quantities may be compared between patients to establish norms or deviation from norm. Without the dose calibration, comparison of activity concentration or uptake over time is subject to variance unrelated to the metabolic function of the patient or patients.

To avoid shipping a source between the reference laboratory and the clinical site, precision sources of the same isotope but different samples are used at both locations. The precision sources have a reference activity for determining the bias at the energy of the isotope of the precision sources. The sample may be different for these long-lived isotopes, but the geometry and/or isotope is the same. A reference source for the isotope of the radiopharmaceutical is provided at the reference laboratory but not the clinical site. The radiopharmaceutical is provided at the clinical site but not the reference laboratory. The sample may be different for these short-lived isotopes, but the geometry and/or isotope is the same.

Additional, different, or fewer acts may be performed. For example, acts 30-33 are for acts performed at the reference laboratory. In alternative embodiments, a table or ratio is provided at the clinical site without performing acts 30-33 for a given radiopharmaceutical. As another example, acts 39 and/or 40 are not provided. In other examples, acts related to positioning, configuring, and/or activating are provided.

The acts are performed in the order shown (top to bottom or numerical) or a different order. For example, acts 30/31, 32/33, and 34/35 are performed simultaneously or in any order (e.g., 32/33 performed before 30/31).

In act 30, a reference gas ion chamber-based or another dose calibrator measures an activity for a source of a long-lived isotope. A pressurized-gas ion chamber measures an activity of the radioisotope sample. The measurement is of the radioisotope sample in the given container with the given geometry. The calibration is geometry and radioisotope specific.

The activity is measured for the total energy deposited by the emissions per unit time. The activity measured includes energy from the primary emissions as well as energy from other gamma and/or X-ray emissions.

The activity is measured at a reference laboratory, such as a manufacturer or facility with a spectroscopic detector. Other locations or facilities remote or different from locations or facilities preparing or using a radiopharmaceutical for patient-based imaging may measure.

Similar measurements are performed in acts 32, 34, and 36 using different sources. Other differences may or may not be provided, such as differences in geometry, location, dose calibrator being used, and/or isotopes.

The source of the long-lived isotope has a known activity level. A Germanium detector, such as a high-purity Germanium detector or other spectroscopic detector, provides the reference activity level. For example, a high-purity Germanium (HPGe), efficiency calibrated HPGe, or other spectroscopic detector measures an activity of the long-lived radioisotope sample. The activity is measured for one or more primary emission energies. For example, the activity for a radioisotope sample of I123 is measured at 159.5 keV and not at other energies. The energies in a range may be measured, such as with tolerance about one or more primary gamma emission energies for the isotope. X-ray energies are not measured. The measure may be activity for one energy window or may be activity in a combination of energies.

The measurement is of a radioisotope sample in a given container with a given geometry. The calibration is geometry and radioisotope specific. Similar reference measurements are provided for the reference sources measured in acts 32 and 34.

In act 31, a processor determines a dial setting from the measured activity for the long-lived isotope sample and the reference or known activity of the long-lived isotope sample. A sensitivity of the gas ion chamber-based dose calibrator that performed the measurement in act 30 for the energy level of the long-lived isotope is determined. A precision source with a long-lived isotope in a fixed geometry is used to determine the DC dial setting of that reference dose calibrator at the energy of the long-lived isotope.

In one embodiment, the reference dose calibrator calibrates the activity of a radioisotope by measuring the total energy deposited by the emissions per unit time and normalizing the measured energy by chamber sensitivity and primary emission branches to compute decays per second (Bq). The reference dose calibrator has an efficiency or sensitivity to the radioisotope. The efficiency accounts for chamber sensitivity and the amount of energy from the primary gamma emissions relative to the other emissions of the isotope. The efficiency correction, sensitivity correction, or dial setting indicates an adjustment or bias to the measurements to account for the difference in sensitivity in detecting emissions at X-ray energies, secondary gamma energies, and primary gamma energies.

The dial setting is a bias representing the difference (e.g., subtraction or ratio) between the measured activity and the reference activity for the long-lived source. In alternative embodiments, the bias or dial setting is known for the reference dose calibrator so measurement of act 30 is not performed. The dial setting or bias is looked up from a table.

Similar determinations are performed in acts 31, 33, and 35 using different sources. Reference activity for the different sources are used to determine the corresponding dial settings of the same or different dose calibrator at the corresponding energy.

In act 32, the reference gas ion chamber-based or another dose calibrator measures an activity of a source of another isotope. The other isotope is the same as the isotope to be used for the radiopharmaceutical, so is a short-lived isotope. The half life is relatively shorter for this isotope than the half life of the isotope measured in acts 30 and 34.

The measurement of the activity is at the same or different location than for the measurement of act 30. For example, the measurement is at the reference laboratory. The location is different than the clinical or pharmacy site.

The measurement is with the source of the isotope in a same geometry to be used for measuring the activity of the radiopharmaceutical in act 36. The geometry may be the same for measuring the sources of the long-lived isotope in acts 30 and 34. A spacer, form, or holder, such as a plastic piece, holds the reference source in a given location within the dose calibrator.

A reference activity of the source with the short-lived isotope is known. A spectroscopic detector or other detector is used to determine the activity of the gamma emissions in the desired band or bands of energy.

In act 33, a processor, such as a processor of the dose calibrator, determines a dial setting from the measured activity of act 32. The sensitivity of the reference dose calibrator to the energy of the short-lived isotope is determined based on the measured activity and the reference activity for the short-lived isotope. A precision container fabricated with low attenuating material of fixed geometry and volume is used to determine the reference dose calibrator dial setting for the short-lived isotope at a reference lab.

In act 34, a clinical gas ion chamber-based or another dose calibrator measures an activity of a precision source of the long-lived isotope. The long-lived isotope is the same as for the reference source measured in act 30, but a different sample is used. The geometry of the source and/or source position in the dose calibrator for the measurement of act 34 is the same as for the measurement of the precision source in act 30. Different activities, volumes, shapes, and/or materials may be used. Preferably, a same volume, shape, and material is provided for both the long-lived isotope sources.

The measurement is at a clinical site, such as a hospital where the functional imaging system is located or a pharmaceutical site where the radiopharmaceutical is created, dispensed, or filled for a patient prescription. The clinical site may be a location of bulk preparation or a dispensary of patient-specific dosages of the radiopharmaceutical. The clinical site is a different location than the location where the reference dose calibrator performs the measurements of acts 30 and 32, but a same location may be used.

The clinical site obtains the precision source of the long-lived isotope and a precision container and repeats the measurement of act 30. The repetition is performed on a different sample of the isotope and by a different dose calibrator than the reference dose calibrator.

The precision source measured in act 34 has a known activity at the energy band or bands of interest. A Germanium (e.g., high-purity Germanium) or other spectroscopic detector at the same or a different reference laboratory provides the reference activity with the source to the clinical site.

In act 35, a processor, such as a processor of the clinical dose calibrator, determines a dial setting from the measured activity of act 34 and the reference activity for that source. The sensitivity of the clinical dose calibrator to the long-lived isotope is determined based on the measured and reference activities for the precision source. The bias or sensitivity correction is determined.

The determination is at the clinical site (e.g., pharmaceutical site or facility of the functional imaging system) but may be at another location. The clinical site obtains a precision source and a precision container and repeats the determination of act 31 but for the local source of the isotope and using the local dose calibrator. The precision source likely already exists at the clinical site for other reasons, so the logistics of shipping the radioactive material every year or two are established.

In act 36, the clinical dose calibrator measures an activity of the radiopharmaceutical. The unit dose, prescribed dose, or bulk dose of the radiopharmaceutical to be used for patient imaging is measured. The isotope in the radiopharmaceutical is the same isotope as the short-lived isotope for the reference source measured in act 32. Different samples using the same isotope are measured by different dose calibrators. The samples are held in the same position within the different dose calibrators. The shape, size, and material of the samples or sources is different or the same. The measurement of act 32 is repeated but for the radiopharmaceutical and with a different dose calibrator (i.e., the clinical dose calibrator instead of the reference dose calibrator).

The measurement of activity of the radiopharmaceutical is subject to the sensitivity of the clinical dose calibrator. Thus, the measurement of activity may be inaccurate or associated with uncertainty.

Since a spectroscopic detector is not available at the clinical site, a processor determines the dial setting for the clinical dose calibrator for the short-lived isotope in act 37. The dial setting is determined from a ratio of dial settings for the reference dose calibrator and the dial setting determined in act 35. The bias determined in act 35 and a ratio of biases are used.

The ratio is of a different dose calibrator's sensitivity to the same long-lived and short-lived isotopes in different samples. The dial settings determined in acts 31 and 33 at the reference laboratory form the ratio. The ratio of the readings of acts 30 and 32 gives a traceable dial setting ratio for the isotope pair as measured at a reference laboratory. The sensitivity of the clinical dose calibrator to the short-lived isotope of the radiopharmaceutical is determined from the sensitivity of that clinical dose calibrator for the long-lived source determined in act 35 and the ratio of the sensitivities of the pair of isotopes (long-lived and short-lived isotopes) from the reference dose calibrator. The ratio of sensitivities, biases, and/or dial settings for one dose calibrator are equal to the ratio for the other dose calibrator. Due to the known activities for three of the sources, the sensitivities for those three sources are determined. These known sensitivities may be used to solve for the unknown sensitivity of the clinical dose calibrator to the short-lived isotope of the radiopharmaceutical. The dial setting or sensitivity correction for the clinical dose calibrator for the radiopharmaceutical being dispensed for SPECT imaging of a patient is calculated.

The determination occurs at the clinical site, such as using a processor of the clinical dose calibrator or a local workstation or computer. Alternatively, a processor at another location uses the measured dial settings from the reference laboratory and a clinical site to determine the dial setting at another location, such as a location of the functional imaging system remote from the clinical dose calibrator.

A table of ratios for isotope pairs may be provided. Results from acts 30-33 for one or more different pairs of isotopes are stored in a table. The same or different reference dose calibrators may have been used for the different pairs. The ratio is looked-up for determining the dial setting for clinical dose calibrator for an available long and short-lived isotope pair. The ratio corresponding to the same combination of long-lived and short-lived isotopes as measured in acts 34 and 36 is accessed or provided. Using the local value for the long-lived precision source dial setting and the ratio from the reference laboratory, a dial setting for the short-lived isotope is derived locally to or for the clinical site.

In act 38, a processor determines a bias from the dial setting and the measured activity. The dial setting may be the bias or the dial setting is used to look-up or determine the bias. The dial setting and/or bias are corrections for the sensitivity of the clinical dose calibrator for the energy of the short-lived isotope of the radiopharmaceutical. The bias is calculated for the radioisotope sample of the radiopharmaceutical. The clinical dose calibrator is calibrated with the dial setting, such as determining the bias to apply to the measured activity of the radiopharmaceutical.

The bias is specific to the geometry and/or isotope in the sample. The calibrations and determination of bias may be repeated for different geometry and isotope combinations. The bias indicates an amount of inaccuracy in the dose from the clinical dose calibrator, so is used to correct.

The radiopharmaceutical may be dispensed and/or labeled with the measured dose. Alternatively, the dose or activity is corrected, and the corrected dose is used to dispense and/or label.

In act 39, a processor corrects the dose value of the radiopharmaceutical using the bias. The bias is determined, and then stored and/or used for calibration of sensitivity. The bias is a correction factor to be applied to any dose for the short-lived isotope measured by the clinical dose calibrator for a given geometry. The measured activity is corrected, removing or reducing inconsistency due to local dose calibrator variation. The correction is a multiplication, division, addition, or subtraction. Other functions may be used. In alternative embodiments, the local correction factor is used to look-up a weight or other adjustment applied to the dose value. In either the direct or indirect sense, the injected dose value for a radiotracer used in a patient is corrected. The correction indicates an amount of error in the dose calibrator measurements, so weights the local dose value. In alternative embodiments, the correction based on the difference in sensitivities is applied to a previously determined local sensitivity.

This approach may be insensitive to the type of emission contamination (e.g., low or high energy background). The correction may be applied in calibrating any isotope regardless of the complexity of the emission spectrum.

The corrected dose based on the bias is used in SPECT, PET, or other functional imaging. A functional imaging system (e.g., SPECT system) estimates the activity concentration. The activity concentration in a patient having received the liquid radiotracer (radiopharmaceutical) is determined as part of reconstruction. After ingesting or injecting the radiopharmaceutical into the patient, the patient is positioned relative to the detector and/or the detector is positioned relative to the patient. Emissions from the radiopharmaceutical within the patient are detected over time.

To determine the locations within the patient at which the emissions occurred, the detected emissions are reconstructed into an object space. Distribution of emissions in a volume or image data is reconstructed. The SPECT imaging system estimates the activity concentration of an injected radiopharmaceutical or tracer for the different locations.

For reconstruction, the activity concentration is reconstructed using a system matrix or model. The reconstruction is iterative and contains a model of the imaging formation physics as a pre-requisite of quantitative reconstruction. The image formation model includes the detected data (e.g., counts), the system matrix or model, isotope properties (e.g., corrected dose value), and biology. The system matrix or model represents mechanical properties of the system, but may include other information (e.g., injection time and patient weight as represented by SUV).

Reconstruction includes a projection operator to simulate a given SPECT system or SPECT class. Any now known or later developed reconstruction methods may be used, such as based on Maximum Likelihood Expectation Maximization (ML-EM), Ordered Subset Expectation Maximization (OSEM), penalized weighted least squares (PWLS), Maximum A Posteriori (MAP), multi-modal reconstruction, NNLS, or another approach.

The imaging physics includes aspects of the SPECT system, such as calibration of the SPECT system. The system matrix or model includes the detector sensitivity, such as the system specific sensitivity to the energy of the liquid radiotracer used in the patient. The corrected dose is included as part of the system matrix or model or as a separate isotope data used in reconstruction. Alternatively or additionally, a corrected sensitivity to account for local dose calibrator variance is used.

In quantitative SPECT, the goal is to estimate the activity concentration as uptake in kBq/ml of the tracer (i.e., isotope) that was injected into and distributed within the patient in act 40. The patient is imaged with a dose based on the bias. The corrected dose value is used in calculating uptake from the activity concentration. Correcting the injected dose may result in more accurate uptake values free of or with reduced local dose calibrator-specific variations.

Specific uptake values (SUVs) are calculated by the processor of the functional imaging system. The activity concentration represents the amount of uptake at each location. This amount of uptake is a measure of emitted radiation, so is not normalized for the radiation dose provided to the patient. As a result, comparing uptake from different times may not be useful unless the same dose is provided. By calculating the SUV, uptake normalized for dose is provided, allowing comparison of different measures.

The SUV for each location or for some of the locations is calculated. The SUV is a function of the activity concentration for that location and the corrected dose. The activity concentration is divided by the corrected injected dose value. Other functions may be used. For example, the SUV may be a function of the body mass or other physical characteristic of the patient. The uptake magnitude represented in the activity concentration is normalized for both dose and body mass.

Due to the calibration for the dose calibrator sensitivity, the SUV may be more accurately compared over time or from different examinations. Different radiotracer doses and/or different detectors may be used. Where the different examinations use the correction for bias, the resulting difference in SUVs more likely represents diagnostic or metabolic difference rather than difference due to variance in detector or dose. Quantification in functional imaging, such as SPECT, provides both accurate activity concentration and accurate SUVs.

FIG. 5 shows a system for functional imaging using corrected dose values. The system includes a SPECT scanner 50, a processor 51, a memory 53, and a display 55. The processor 51, memory 53, and/or display 55 are part of the SPECT scanner 50 or are separate (e.g., a computer or workstation). The processor 51, memory 53, and/or display 55 may be the processor 12, memory 14, and/or display 16, respectively of FIG. 2 or are separate devices. Additional, different, or fewer components may be provided. For example, the system is a computer without the SPECT scanner 50. As another example, user input, patient bed, or other SPECT related devices are provided. Other parts of the system may include power supplies, communications systems, and user interface systems. In yet another example, a PET scanner or other functional imaging system is provided instead of the SPECT scanner 50.

The SPECT scanner 50 is a SPECT system. As a SPECT system, a detector 58 is provided. Other components may be provided, such as collimator. Any now known or later developed SPECT scanner 50 may be used. The detector 58 is a gamma camera connected with a gantry. The gamma camera is a planar photon detector, such as having crystals or scintillators with an optical detector. The gantry rotates the gamma camera about the patient. During scanning of a patient, emission events are detected with the camera at different positions or angles relative to the patient. The emission events are from a radiotracer 57 in the patient.

The SPECT scanner 50, using the detector 58, detects emissions from the radiotracer 57. The radiotracer 57 is the radiopharmaceutical 26 so shares a radioisotope and geometry with the short-lived source 23 but may be a different sample from a different or same lab. For imaging uptake in a patient, the detector 58 detects emissions from the patient. The emissions occur from any location in a finite source (i.e., the patient). The radiotracer 57 in the patient migrates to, connects with, or otherwise concentrates at specific types of tissue or locations associated with specific biochemical reactions. As a result, a greater number of emissions occur from locations of that type of tissue or reaction. For example, the radiotracer 57 is designed to link with locations of glucose uptake, fatty acid synthesis, or other metabolic process.

The SPECT scanner 50 is configured to reconstruct the imaged volume by applying a system matrix or model to the detected data. The processor 51 is used to perform the reconstruction, or the SPECT scanner 50 has another processor that performs the reconstruction. Any reconstruction may be used to estimate the activity concentration in the patient. The SPECT scanner 50 accesses the detected emission events from the memory 53 or buffers to reconstruct. The system matrix or model includes a system sensitivity for the liquid radiotracer provided to the patient. This sensitivity is used for the reconstruction. Differences between the local calibrated sensitivity and a factory calibrated sensitivity based on the bias corrected dose are used to correct for dose calibration measurements. The reconstruction also uses a sensitivity-based correction of dose value for the radiotracer applied to the patient. The corrected dose is used.

The processor 51 is configured by software, firmware, and/or hardware. The processor 51 operates pursuant to stored instructions to perform various acts described herein, such as correcting of act 39 and the calculation of SUV of act 40. The processor 51 receives, looks-up, or accesses a bias or a calibrated sensitivity for a given isotope and geometry corresponding to the isotope and geometry of the radiotracer 57 to be used in the patient. The processor 51 uses the bias to correct the dose from the dose calibrator. For a patient scan, the processor 51 uses the bias correction to determine a local correction for the dose. The processor 51 may correct a dose value for the radiotracer 57 using a correction based on a difference between the calibrated sensitivity and the measured sensitivity. The processor 51 is configured to correct the input dose of the liquid radiotracer provided to the patient. For example, the ratio of sensitivities is multiplied with the dose. Based on this corrected dose, the processor 51 is configured to reconstruct activity concentration and/or calculate SUVs. The SUV at one or more locations are calculated by normalizing the activity concentration with the corrected dose. The resulting SUVs have less variability due to the system and/or dose, so more likely represent changes in metabolic function of the patient.

The bias, dose value, scan data, sensitivities, corrected dose, measured activity, efficiencies, and/or other information are stored in the memory 53 and/or 14. The data is stored in any format. The memories 53, 14 are a buffer, cache, RAM, removable media, hard drive, magnetic, optical, database, or other now known or later developed memory. Each of the memories 53, 14 is a single device or group of two or more devices. In one embodiment, the memory 53 stores a table of ratios, biases, dial settings, sensitivities, and/or corrections based on differences in sensitivities as a function of isotope and geometry. The table is transferred to the memory 53 of a functional imaging system for use in correcting dose from a dose calibrator local to the SPECT scanner 50.

The memories 53, 14 are additionally or alternatively a non-transitory computer readable storage medium with processing instructions. The memories 53, 14 store data representing instructions executable by the programmed processors 11, 52, respectively. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The displays 55, 16 are a CRT, LCD, plasma screen, projector, printer, or other output device for showing an image. The display 16 displays a bias, dose, sensitivity, measured activity, and/or corrected dose. The display 55 displays an image of the reconstructed functional volume, such as showing activity concentration as a function of location. The uptake function of the tissues of the patient is represented in the image. Multiplanar reconstruction, 3D rendering, or cross-section imaging may be used to generate the image from the voxels of the reconstructed volume. The corrected dose may be displayed as an annotation with the image.

Alternatively or additionally, any quantities derived by the processor 51 may be displayed, such as corrected dose, dose and bias, sensitivity, SUVs, and/or change in SUV. Other quantities may be determined, such as average SUV or activity concentration for a region, maximum SUV, peak SUV in a predetermined unit volume, variance in activity concentration, or total SUV.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method of dose calibration for a functional imaging system, the method comprising:
    measuring (30) a first activity for a first source of a first isotope with a first dose calibrator (20) at a first location;
    determining (31) a first dial setting from the first activity;
    measuring (32) a second activity of a second source of a second isotope with the first dose calibrator (20) at the first location, the second isotope being relatively shorter lived than the first isotope;
    determining (33) a second dial setting from the second activity;
    measuring (34) a third activity of a third source of the first isotope with a second dose calibrator (24) at a second location, the second location being a clinical or pharmaceutical site different than the first location;
    determining (35) a third dial setting from the third activity;
    determining (37) a fourth dial setting for a radiopharmaceutical (26) of the second isotope from the third dial setting and a ratio of the first dial setting to the second dial setting;
    measuring (36) a fourth activity of the radiopharmaceutical (26); and
    calibrating (39) the fourth activity with the fourth dial setting.

2. The method of claim 1 wherein measuring (30, 34) the first and third activities comprises measuring (30, 34) with the first and third sources having activity levels determined from a high-purity Germanium detector.

3. The method of claim 1 wherein measuring (30, 34) the first and third activities comprises measuring (30, 34) with the first and third sources being of different samples of the same first isotope.

4. The method of claim 1 wherein measuring (30, 34) the first and third activities comprises measuring (30, 34) with the first and third sources held in a same position within the first and second dose calibrators (20, 24), respectively, and measuring (32, 36) the second and fourth activities comprises measuring (32, 36) with the second source and the radiopharmaceutical (26) held in a same position within the first dose calibrator (20) and a third dose calibrator, respectively.

5. The method of claim 1 wherein measuring (30, 32) the first and second activities at the first location comprises measuring (30, 32) at a reference laboratory.

6. The method of claim 1 wherein determining (31, 33, 35) the first, second, and third dial settings comprises determining (31, 33, 35) a sensitivity based on the measured first, second, and third activities and reference activities of the first, second, and third sources, respectively.

7. The method of claim 1 wherein determining (37) the fourth dial setting comprises determining (37) the fourth dial setting for the radiopharmaceutical (26) being dispensed for single photon emission computed tomography (SPECT) imaging of a patient.

8. The method of claim 7 wherein calibrating (39) comprises determining (38) a bias for the radiopharmaceutical (26), and further comprising SPECT imaging the patient with a dose based on the bias.

9. The method of claim 1 wherein measuring (36) the fourth activity comprises measuring (36) the fourth activity with the radiopharmaceutical (26) having a sample of the second isotope.

10. The method of claim 1 wherein measuring (32) the second activity comprises measuring (32) with the second isotope having a half life of one week or less and with the first isotope having a half life of one year or more.

11. The method of claim 1 wherein determining (35, 37) the third and fourth dial settings comprises determining at the clinical or pharmaceutical site.

12. A method of dose calibration for a functional medical imaging system, the method comprising:
   measuring (34) a first activity of a first source of a first isotope with a first dose calibrator (24) at a clinical or pharmaceutical site;
   determining (35) a first sensitivity of the first dose calibrator (24) to the first isotope from the first activity and a reference activity of the first source;
   determining (37) a second sensitivity of the first dose calibrator (24) to a second isotope from the first sensitivity and a ratio of third and fourth sensitivities of a second dose calibrator (20) to the first isotope and the second isotope, respectively; and
   measuring (36) a radiopharmaceutical activity of a radiopharmaceutical (26) of the second isotope with the second sensitivity.

13. The method of claim 12 wherein determining (37) the second sensitivity comprises determining (37) with the ratio being from a table of isotope pairs, the ratio being for one of the isotope pairs being for the first and second isotopes.

14. The method of claim 12 wherein the first isotope has a half life of at least six months, wherein the second isotope has a half life of less than one month, and wherein measuring (34) the first activity comprises measuring (34) with the reference activity of the first source being from a Germanium detector.

15. The method of claim 12 wherein determining (37) the second sensitivity comprises determining (37) a dial setting of the first dose calibrator (24).

16. The method of claim 12 wherein determining (37) the second sensitivity comprises determining (37) with the ratio being from a reference laboratory, and wherein measuring (34) the first activity comprises measuring (34) at the clinical or pharmaceutical site comprising a dispensary for patient dosages of the radiopharmaceutical (26).

17. The method of claim 12 wherein measuring (36) the radiopharmaceutical activity comprises measuring (36) a dose of the radiopharmaceutical (26), and further comprising labeling the radiopharmaceutical (26) with the dose.

18. A system for calibration of dose in functional imaging, the system comprising:
   a radiotracer source (25) with a reference activity;
   a first gas ion chamber-based dose calibrator (24) for measuring activity of the radiotracer source (25) and activity of a radiopharmaceutical (26); and
   a processor (12) configured to determine a bias of the activity of the radiopharmaceutical (26) by the first gas ion chamber-based dose calibrator (24) from (1) a first dial setting of the first gas ion chamber-based dose calibrator (24) determined from the activity of the radiotracer source (25) and the reference activity and (2) a ratio of second and third dial settings for an isotope of the radiotracer source (25) to isotope of the radiopharmaceutical (26).

19. The system of claim 18 wherein the ratio is based on measurement from a second gas ion chamber-based dose calibrator (20) at a reference laboratory and wherein the reference activity is based on measurement by a high-purity Germanium detector.

20. The system of claim 18 wherein the processor (12) is configured to determine a dose of the radiopharmaceutical (26) from the bias of the activity of the radiopharmaceutical (26).

* * * * *